(12) United States Patent
Müller et al.

(10) Patent No.: US 9,244,064 B2
(45) Date of Patent: *Jan. 26, 2016

(54) USE OF HYDROGELS FOR BIOSENSORS HAVING ELEVATED SENSITIVITY

(75) Inventors: Achim Müller, Grossostheim (DE); Peter Herbrechtsmeier, Königstein (DE); Monika Knuth, Goldbach (DE); Katharina Nikolaus, Aschaffenburg (DE)

(73) Assignee: EYESENSE AG, Basel (CH)

( * ) Notice: Subject to any disclaimer, the term of this patent is extended or adjusted under 35 U.S.C. 154(b) by 44 days.

This patent is subject to a terminal disclaimer.

(21) Appl. No.: 13/994,071

(22) PCT Filed: Dec. 13, 2011

(86) PCT No.: PCT/EP2011/072622
§ 371 (c)(1),
(2), (4) Date: Sep. 25, 2013

(87) PCT Pub. No.: WO2012/080258
PCT Pub. Date: Jun. 21, 2012

(65) Prior Publication Data
US 2014/0024060 A1 Jan. 23, 2014

(30) Foreign Application Priority Data
Dec. 17, 2010 (EP) .................................... 10195668

(51) Int. Cl.
*G01N 33/53* (2006.01)
*G01N 33/66* (2006.01)

(52) U.S. Cl.
CPC ............ *G01N 33/5308* (2013.01); *G01N 33/66* (2013.01)

(58) Field of Classification Search
None
See application file for complete search history.

(56) References Cited

U.S. PATENT DOCUMENTS

| | | | |
|---|---|---|---|
| 6,485,703 | B1 | 11/2002 | Cote et al. |
| 7,439,080 | B2 | 10/2008 | Hoenes et al. |
| 2007/0105176 | A1 | 5/2007 | Ibey et al. |
| 2007/0122829 | A1 | 5/2007 | Ballerstadt et al. |
| 2010/0331634 | A1 | 12/2010 | Müller et al. |

FOREIGN PATENT DOCUMENTS

| | | |
|---|---|---|
| EP | 1 705 485 A1 | 9/2006 |
| EP | 2 052 677 A1 | 4/2009 |
| WO | WO 01/13783 A1 | 3/2001 |
| WO | WO 01/16575 A1 | 3/2001 |
| WO | WO 02/087429 A1 | 11/2002 |
| WO | WO 2006/061207 A1 | 6/2006 |
| WO | WO 2007/065653 A1 | 6/2007 |
| WO | WO 2008/142158 A2 | 11/2008 |

OTHER PUBLICATIONS

Rounds et al., "Microporated PEG Spheres for Fluorescent Analyte Detection," *J. Fluoresc.*, vol. 17, pp. 57-63 (2007).
Moothoo et al., "Man α1-2 Man α-OMe-concanavalin A complex reveals a balance of forces involved in carbohydrate recognition," *Glycobiology*, vol. 9, No. 6, pp. 539-545 (1999).
Bryce et al., "Carbohydrate-Protein Recognition: Molecular Dynamics Simulations and Free Energy Analysis of Oligosaccharide Binding to Concanavalin A," *Biophysical Journal*, vol. 81, pp. 1373-1388 (2001).
Moothoo et al., "Concanavalin A distorts the β-GlcNAc-(1-2) Man Linkage of β-GlcNAc-(1-2)-α-Man-(1-3)-[α-GlcNAc-(1-2)-α-Man-(1-6)]-Man upon binding," *Glycobiology*, vol. 8, No. 2, pp. 173-181 (1998).
Delatorre et al., "Structure of a lectin from Canavalia gladiata seeds: new structural insights for old molecules," *BMC Structural Biology*, vol. 7, No. 52, pp. 1-9 (2007).
Rolinski et al., "Molecular distribution sensing in a fluorescence resonance energy transfer based affinity assay for glucose," *Spectrochimica Acta Part A*, vol. 57, pp. 2245-2254 (2001).
Yamauchi et al., "Structure of the gene encoding concanavalin A from Canavalia gladiata and its expression in *Escherichia coli* cells," vol. 260, No. 1, pp. 127-130 (1990).
Cheung et al., "Reusable optical bioassay platform with permeability-controlled hydrogel pads for selective saccharide detection," *Analytica Chimica Acta*, vol. 607, pp. 204-210 (2008).
International Preliminary Report on Patentability issued in related International Patent Application No. PCT/EP2011/072622, dated Jun. 27, 2013.

*Primary Examiner* — Suzanne M Noakes
(74) *Attorney, Agent, or Firm* — Foley & Lardner LLP

(57) ABSTRACT

The present invention relates to measures for determining glucose and for diagnosing diseases based on impaired glucose metabolism. In particular the present invention relates to the use of a polymer-based hydrogel consisting of at least one water-soluble polymer in a sensor for enriching a dissolved glucose-binding protein, wherein the at least one water-soluble polymer is capable of interacting with the glucose-binding protein and wherein the glucose-binding protein is present in a complex with a ligand.

12 Claims, No Drawings

USE OF HYDROGELS FOR BIOSENSORS HAVING ELEVATED SENSITIVITY

The present invention relates to the use of a polymer-based hydrogel comprising at least one water-soluble polymer in a sensor for enriching a dissolved glucose-binding protein, wherein the at least one water-soluble polymer is capable of interacting with the glucose-binding protein and wherein the glucose-binding protein is present in a complex with a ligand.

The determination of the concentration of glucose by efficient and reliable measurement technology is of great importance in many fields of technology. Not only in pure laboratory analysis, but also in the foodstuffs industry, e.g. in the field of oenology and in the medical field, for example in the diagnosis of diseases which are caused by impaired glucose metabolism, e.g. diabetes mellitus or metabolic syndrome, the rapid and reliable determination of the glucose concentration in given solutions is of central importance. In the field of the diagnosis of diseases that are based on impaired glucose metabolism, glucose sensors are used both in devices which are implantable into the body and can measure the glucose content in a sample taken within the body, and also in sensors that measure the glucose content ex vivo from a test subject's sample.

For determining the glucose content in a solution, systems made of sensor molecule and ligand have been described, wherein the sensor is a glucose-binding protein and the ligand a competitor for glucose, which is initially present in the sensor bound to the glucose sensor molecule. By competition with glucose during the measurement procedure, the competitor is displaced from the glucose-binding protein. The displacement of the competitor from the glucose-binding protein by the glucose during this can be detected by means of a change in a physical or chemical property of the molecules, e.g. by means of fluorescence resonance energy transfer (FRET). The aforesaid systems must of course be present in a spatially demarcated region of the sensor.

For enclosure of the system components, i.e. of the glucose-binding molecule and the ligand, in an aqueous medium, semi-permeable membranes are used. Such membranes can for example consist of regenerated cellulose, polyethylene glycol, polyurethane, layer-by-layer (LBL) layers, polyether sulfones, parylene layers or perforated silica (e.g. US2007/0122829). Alternatively, hydrogels, which are however usually also enclosed by an additional membrane, can also be used (see e.g. U.S. Pat. No. 6,485,703; US2007/0105176).

However, the glucose sensors described in the state of the art exhibit relatively low glucose activity. The glucose activity and hence the sensor performance is predominantly determined by the binding constants for the complex of glucose-binding protein and competitor and glucose-binding protein and glucose. Furthermore, the mobility of the sensor components also plays a part. In hydrogel matrices, this is rather restricted (Rounds 2007, J. Fluoresc. 17: 57-63).

With in vivo sensors for measuring glucose, the sensor must constantly react reversibly to changes in the analyte concentration. Thus the binding constant must not be too high, since otherwise the sensor would already be saturated at low analyte concentrations, and would no longer be able to indicate concentration changes. Moreover, a further problem of the in vivo sensors consists in that the analyte concentration range is fixed and cannot be optimized by dilution or concentration. Essentially, in the state of the art, systems consisting of ligand and glucose-binding protein are described wherein medium binding constants are implemented. Adaptation of the measurement sensitivities by alteration of the concentrations of either glucose-binding protein or ligand or both (e.g. by enrichment) are as a rule limited by the low solubility of the respective molecules. Hence in the sensors described in the aforesaid state of the art, both the measurement sensitivity and also the measurement precision of the sensor are limited.

The purpose of the present invention is to provide measures which make it possible to improve the measurement sensitivity and precision of biosensors for measurement of the glucose level. The invention is solved by the embodiments described by the claims and the embodiments which are disclosed below.

The present invention thus relates to the use of a polymer-based hydrogel comprising at least one water-soluble polymer in a sensor for enriching a dissolved glucose-binding protein, wherein the at least one water-soluble polymer is capable of interacting with the glucose-binding protein and wherein the glucose-binding protein is present in a complex with a ligand.

The term "hydrogel" describes a water-containing polymer whose molecules are chemically or physically linked into a three-dimensional network. The polymer molecules can be linked together into the three-dimensional network by covalent or ionic bonds or by entanglement or interweaving. The polymers which form the hydrogel preferably contain hydrophilic polymer components which enable the uptake of aqueous solutions, and groups which are capable of interacting with the glucose-binding protein. In particular for lectins such as concanavalin A, as well as a binding site for monosaccharides, e.g. glucose, a further binding site for terminal sugar molecules has also been described (Moothoo 1999, Glycobiology 9(6): 539-545; Bryce 2001, Biophysical Journal 81: 1373-1388; Moothoo 1998, Glycobiology 8(2): 173-181; Delatorre 2007, BMC Structural Biology 7:52). Sugar or structurally similar molecules or residues in the polymer molecules of the hydrogel are preferably capable of interacting with this further binding site. Depending on the nature of the glucose-binding protein, according to the invention a polymer is selected which has residues which are capable of interacting with the glucose-binding protein, without thereby blocking the binding site for glucose. Suitable residues for this can also be antibodies or antibody fragments, such as Fab $F(ab)_2$, $scF_V$ or the like, which are coupled to the polymer, and which specifically recognize the glucose-binding protein. Aptamers can also be used instead of antibodies in an analogous manner, which specifically recognise the glucose-binding protein.

Preferably the at least one polymer is selected from the group consisting of: alginates, sepharose, hyaluronic acid, chitosan, caragenans, polyvinyl alcohols (PVAs), polyethylene glycols (PEGs), poly(2-oxazolines), polyacrylamides (e.g. dimethylacrylamide), polyhydroxyacrylates (e.g. polyhydroxymethacrylate, polyhydroxyacrylamides, polyvinylpyrolinones), (2-methyl-3-ethyl[2-hydroxyethyl]) polymers, polyhydroxyalkanoates (PHAs), poly(2-methyl-2 oxazolines), poly(2-ethyl-2 oxazolines), poly(2-hydroxyethyl-2 oxazolines), poly(2-(1-(hydroxymethyl)-ethyl)-2 oxazolines), poly-(hydroxyethyl methacrylate) (PHEMA), poly-(hydroxyethyl acrylate) (PHEA), poly-vinylpyrolidones, poly-(dimethyl)acrylamide, poly-(hydroxyethyl) acrylamide, polyvinyl alcohols (including copolymers with vinyl acetates and/or ethylene), poly(ethylene-co-vinyl alcohol), poly(vinyl acetate-co-vinyl alcohol), poly(ethylene-co-vinyl acetate-co-vinyl alcohol), polyethylene glycols and poly(ethylene glycol-co-propylene glycol).

Particularly preferably, the at least one polymer is selected from the group consisting of: alginates, sepharose, hyaluronic acid, chitosan, and caragenans. Quite particularly preferably, the at least one polymer is an alginate.

It goes without saying that the hydrogel in the sensor can contain yet further polymers. In particular, the polymer-based hydrogel can comprise a first hydrogel matrix made of alginate and a second hydrogel matrix which is capable of forming an interpenetrating network within the first hydrogel matrix. This second hydrogel matrix preferably consists of a water-soluble polymer having at least one crosslinkable group per molecule and a molecular weight of at most 500,000. Particularly preferable is a molecular weight of at most 250,000, 200,000, 150,000, 100,000 or 50,000. In this, the polymer of the second hydrogel matrix is preferably selected from the group consisting of: polyvinyl alcohols (PVAs), polyethylene glycols (PEGs), poly(2-oxazolines), polyacrylamides (e.g. dimethylacrylamide), polyhydroxyacrylates (e.g. polyhydroxymethacrylate, polyhydroxyacrylamide, polyvinylpyrolinones), (2-methyl-3-ethyl[2-hydroxyethyl]) polymers, polyhydroxyalkanoates (PHAs), poly(2-methyl-2 oxazolines), poly(2-ethyl-2 oxazolines), poly(2-hydroxyethyl-2 oxazolines), poly(2-(1-(hydroxymethyl)-ethyl)-2 oxazolines), poly-(hydroxyethyl methacrylate) (PHEMA), poly-(hydroxyethyl acrylate) (PHEA), polyvinylpyrolidones, poly-(dimethyl)acrylamide, poly-(hydroxyethyl) acrylamide, polyvinyl alcohols (including copolymers with vinyl acetates and/or ethylene), poly(ethylene-co-vinyl alcohol), poly(vinyl acetate-co-vinyl alcohol), poly(ethylene-co-vinyl acetate-co-vinyl alcohol), polyethylene glycols and poly(ethylene glycol-co-propylene glycol).

Particularly preferably, the second hydrogel matrix is formed of polyvinyl alcohol. Particularly preferred is polyvinyl alcohol having a molecular weight of 10,000 to 100,000, more preferably 10,000 to 50,000, more preferably 10,000 to 20,000, and quite particularly preferably 15,000. Particularly preferably, the polyvinyl alcohol has a crosslinker content of at most 0.5 mmol/g, 0.4 mmol/g, 0.35 mmol/g, or 0.3 mmol/g and quite particularly preferably 0.35 mmol/g. Furthermore, the polyvinyl alcohol particularly preferably has a prepolymer solids content of less than 40 weight percent.

As well as the first hydrogel matrix and the second hydrogel matrix, the hydrogel according to the invention can contain additives, e.g. stabilizers, emulsifiers, antioxidants, UV stabilizers, detergents and/or UV initiators.

The hydrogel used according to the invention can moreover be enclosed by a further, preferably semipermeable, covering material. By means of this enclosure, "leaching" of the sensor components from the hydrogel is prevented. Possible covering materials are semipermeable membranes or other hydrogel matrices. Semipermeable membranes can preferably consist of regenerated cellulose, polyethylene glycol, polyurethane, layer-by-layer (LBL) layers, polyether sulfones, parylene layers or perforated silica. However, a further hydrogel matrix is also possible as covering material. Preferably, this can be formed from a polymer selected from the group consisting of alginates, sepharoses, hyaluronic acid, chitosan, caragenans, polyvinyl alcohols (PVAs), polyethylene glycols (PEGs), poly(2-oxazolines), polyacrylamides (e.g. dimethylacrylamide), polyhydroxyacrylates (e.g. polyhydroxymethacrylate, polyhydroxyacrylamides, polyvinylpyrolinones), (2-methyl-3-ethyl[2-hydroxyethyl]) polymers, polyhydroxyalkanoates (PHAs), poly(2-methyl-2 oxazolines), poly(2-ethyl-2 oxazolines), poly(2-hydroxyethyl-2 oxazolines), poly(2-(1-(hydroxymethyl)-ethyl)-2 oxazolines), poly-(hydroxyethyl methacrylate) (PHEMA), poly-(hydroxyethyl acrylate) (PHEA), poly-vinylpyrolidones, poly-(dimethyl)acrylamide, poly-(hydroxyethyl) acrylamide, polyvinyl alcohols (including copolymers with vinylacetates and/or ethylene), poly(ethylene-co-vinyl alcohol), poly(vinyl acetate-co-vinyl alcohol), poly(ethylene-co-vinyl acetate-co-vinyl alcohol), polyethylene glycols and poly(ethylene glycol-co-propylene glycol).

The term "glucose-binding protein" in the context of the invention relates to proteins which are capable of interacting specifically with glucose. Whether a protein is capable of interacting specifically with glucose can readily be determined by those skilled in the art by binding tests known in the state of the art. Preferably, the glucose-binding protein is also capable of interacting with the polymer of the hydrogel. Preferably, this interaction is not mediated by the glucose-binding site of the glucose-binding protein. Particularly preferably, the glucose-binding protein is selected from the group consisting of lectins, enzymes which bind glucose as substrate, and antibodies which specifically recognize glucose. The term also includes surrogate molecules which can specifically recognize glucose, preferably aptamers which specifically recognize glucose. Quite particularly preferably, the glucose-binding protein is concanavalin A.

Nucleic acid sequences and amino acid sequences which encode the aforesaid glucose-binding proteins are known in the state of the art (Yamauchi 1990, FEBS Letters 260(1): 127-130). Accordingly, the aforesaid proteins can readily be prepared by those skilled in the art. Said proteins can for example be prepared recombinantly or be purified from a biological source. Furthermore, the proteins can also be chemically synthesized. Moreover, most of the aforesaid proteins are commercially available. Antibodies or aptamers which specifically recognize glucose can readily be prepared by those skilled in the art by methods for antibody or aptamer obtention known in the state of the art.

The aforesaid glucose-binding proteins and in particular concanavalin A can preferably also have chemical modifications which mediate increased water solubility compared to unmodified versions of the glucose-binding proteins. Such modifications preferably comprise functionalization with a water-soluble polymer and in a particularly preferable embodiment can be selected from the group consisting of: pegylation, acetylation, polyoxazolinylation and succinylation.

The detection of glucose in a sample for analysis is effected in the device according to the invention by displacement of the ligand bound to the glucose-binding protein by the glucose contained in the sample (competition between ligand and glucose). Hence the ligand preferably has a lower affinity to the glucose-binding protein than glucose. The displacement can preferably be detected by labeling of the ligand with a dye or another detectable marker molecule. Dyes or other marker molecules which on approach of the molecules bound to them cause a change in at least one measurable physical or chemical property have proved particularly suitable for the detection of a displacement. Suitable systems include those in which a measurable signal is either suppressed or generated by means of energy transfer between the dye molecules. Such energy transfer-based systems are for example described in more detail in WO2001/13783. These can preferably be systems in which a fluorescence signal is suppressed by quenching effects when the dye or marker molecules—and hence the glucose binding protein and its ligand—are in spatial proximity. After the displacement of the ligand by the analyte, the quenching effect is then canceled. This effect is detectable by a change in the fluorescence. For the detection, for example fluorescence photometers as described in WO2002/087429 can be used. Other suitable systems are so-called fluorescence resonance energy transfer (FRET)-based detection systems. In these, two interacting components, such as the glucose-binding protein and its ligand, are labeled with fluorescent dyes. One component is coupled with an acceptor dye, the other with a donor dye. Through the interaction of the components, the dyes come into spatial proximity, whereby the FRET effect is produced. In this, excitation energy is transferred from the donor to the acceptor dye and thus the intensity of the donor dye is measurably decreased. As soon as the interaction of the components is interrupted, the fluorescent intensity of the donor again increases. In the case of the device according to the invention, the glucose can thus be detected via the increase in the intensity of a signal which is generated by a dye or marker molecule after separation of the complex of glucose-binding protein and ligand by the analyte. The dye or the marker molecule is coupled either to the glucose-binding protein or the ligand. For example, a donor dye can be coupled to the glucose-binding protein or the ligand, while the component not coupled to the donor dye is coupled to a suitable acceptor dye. In a thus configured device according to the invention, the FRET effect as a result of the binding of the ligand to the glucose-binding protein can be observed before exposure to a glucose-containing sample. After exposure, the glucose displaces the ligand, so that the measurable intensity of the fluorescence of the donor dye increases, in fact proportionately to the quantity of glucose.

Birch et al. (Birch 2001, Spectrochimica Acta Part A 57: 2245-2254) have calculated the mathematical solution of the chemical equilibrium for the case of concanavalin A as glucose-binding protein and dextran as ligand. Simulations with varying concanavalin A and dextran concentrations have shown that the ratio (dextran)/(Con A-dextran complex) depends only slightly on the starting concentrations and that the binding constants $K_{Dex}$ and $K_{Gluc}$ are the main factors for sensor performance.

Surprisingly, however, the structure of the dyes also affects the glucose activity. Thus according to the invention a combination of a rhodamine and an oxazine dye is markedly superior to the conventionally used combination of a xanthene and a rhodamine dye (FITC-TMR).

Preferably, the glucose-binding protein which is used in the context of the use according to the invention is linked to an oxazine dye. How such a linkage can be effected is well known to those skilled in the art and adequately described in the state of the art. Particularly preferably, the oxazine dye is an oxazine acceptor selected from the group consisting of: ATTO655, ATTO680, EVOblue10, EVOblue30, EVOblue90 and EVOblue100. Quite particularly preferably, ATTO680 is used. Said oxazine dyes are commercially available.

The preferred degree of labeling (DOL) for the glucose-binding protein, e.g. concanavalin A, is 0.1 to 4, more preferably 1 to 4 and particularly preferably 1 to 3. With concanavalin A, a DOL of 1 here corresponds to one mol of dye per mole of concanavalin A tetramer (MW=104,000). With a high DOL and use of relatively nonpolar dyes (typically long wavelength fluorescent dyes) the glucose-binding protein is preferably functionalized with PEG. The preferred degree of pegylation is 0.1 to 5, preferred molecular weight 200 to 10,000, particularly preferably 800 to 8000, still more preferably 800 to 5000.

In the context of the experiments on which the present invention is based, it was established that chemical modifications of the glucose-binding proteins which mediate increased water-solubility in comparison to unmodified forms can advantageously be used in order to achieve a better degree of labeling on the glucose-binding proteins. For the modified glucose-binding proteins according to the present invention, higher degrees of labeling with a dye can also be achieved than for unmodified forms thereof. For such modified concanavalin A proteins, concentrations preferably greater than 0.5 mg/(g matrix) and quite particularly preferably between 2 and 60 mg/(g matrix) can be achieved. Surprisingly, the measured glucose activity of modified concanavalin A proteins here was also comparable with that of native concanavalin A in hydrogel.

In this, the dissolved glucose-binding protein can be present in the hydrogel at an at least 5-fold, at least 10-fold, at least 15-fold or at least 20-fold elevated concentration compared with an aqueous solution.

The improved solubility is particularly relevant when the glucose-binding proteins are to be labeled with a dye, since glucose-binding proteins labeled with dyes, for example a concanavalin A modified with one of the aforesaid oxazine dyes, have still further reduced solubility in aqueous solution. Here, the higher the degree of labeling is, the lower is the solubility in aqueous solution. However, it is precisely a higher degree of labeling that is needed for glucose-binding proteins as sensor components in the devices according to the invention.

The term "ligand of the glucose-binding protein" means a molecule which is capable of entering into specific bonding with the glucose-binding protein, during which the molecule essentially interacts with the same binding site as glucose, so that the bound molecule can be displaced from the binding site on the glucose-binding protein by glucose. Molecules suitable as the ligand are therefore structurally related to glucose. The ligand of the glucose-binding protein is preferably an oligosaccharide, a glycosylated macromolecule, e.g. a glycosylated protein or peptide, or a glycosylated nanoparticle. The aforesaid molecules which can be used as ligands of the glucose-binding protein are known in the state of the art and can readily be prepared by those skilled in the art. Particularly preferably, a dextran is used as ligand of the glucose-binding protein.

The ligand of the glucose-binding protein in the sensor is preferably coupled with a rhodamine dye. Particularly preferably, ATTO590, ATTO610, ROX, TMR, rhodamine G6, Alexa Fluor rhodamine dyes or Dy590, and quite particularly preferably ATTO590, can be used in this.

The preferred degree of labeling (DOL) for the ligand of the glucose-binding protein, e.g. dextran, is 0.00003 to 0.017 (mol dye)/(mol subunit), particularly preferably 0.0005 to 0.007 (mol dye)/(mol subunit) and quite particularly preferably 0.001 to 0.0016 (mol dye)/(mol subunit). The degree of labeling of the ligand also has an influence on the glucose activity. Excessively low, just like excessively high, degrees of labeling lead to poor glucose activity.

In a preferred embodiment of the use according to the invention, the glucose-binding protein is concanavalin A. Likewise, through chemical modifications, preferably pegylation, acetylation, polyoxazolinylation or succinylation, the concanavalin A exhibits increased water-solubility compared to the unmodified concanavalin A. In a preferred embodiment, the glucose-binding protein is linked to an oxazine dye and the ligand of the glucose-binding protein to a rhodamine dye. Quite particularly preferably, a concanavalin A/dextran system is used in the sensor device, wherein the dextran is linked to a rhodamine donor dye and the concanavalin A to an oxazine acceptor dye. In the preferred concanavalin A/dextran system, the components are preferably present in a mass ratio (dextran/ConA) from 1:1 to 1:40, with mass ratios close to 1:10 being particularly preferable.

In the context of the present invention, it was ascertained that the combination of oxazine and rhodamine dyes causes a heterodimeric interaction between the dye residues, which intensifies the glucose activity. Thus through the use of oxazine acceptor and rhodamine donor dyes, a 2.1-fold glucose activity can preferably already be achieved in aqueous solution. In the hydrogel used in the context of the present invention, a 2.6-fold increase in the glucose activity could even be produced.

Through the use of a polymer which is capable of interacting with the glucose-binding protein, a higher concentration of glucose-binding protein and ligand in the hydrogel can be achieved. This increases the measurement sensitivity but also the measurement precision of the sensor, in particular with in vivo applications with given glucose concentration.

In the context of the present invention, it was advantageously ascertained that the use of a hydrogel consisting of a first hydrogel matrix made of alginate and a second hydrogel matrix which forms an interpenetrating network within the first is capable of creating an environment for the sensor components, namely the glucose-binding protein and the competitive ligands of the glucose-binding protein, which allows efficient determination of the glucose activity. Many approaches for glucose measurement by means of fluorescence are successful in solution, but lose their activity when the sensor components are embedded in hydrogel matrices, since the mobility of the sensor components is restricted (Rounds 2007, J. Fluoresc. 17: 57-63; US 2007/0105176 A1). Surprisingly, however, particularly also in view of the calculations of Birch et al. (Birch 2001, loc cit.), activity increased by up to 2.6-fold compared to aqueous solutions could be detected in the present case. Through the selection of suitable hydrogel matrices, an enrichment of the glucose-binding protein far above its solubility limit in aqueous solution could be achieved. In the case of concanavalin A, for example a more than 10-fold increased concentration compared to a concentration achievable in free solution could be achieved. Usually, the solubility of the receptor component in free solution is further adversely influenced by the addition of the ligand, since the receptor/competitor complex exhibits a lower solubility owing to its size and often also owing to multivalences. While for example a concanavalin A/dextran complex in solution at a mass ratio of 1:10 already begins to precipitate beyond a concanavalin A concentration of 0.5 mg/(g solution), in a suitable hydrogel with the same mass ratio, concanavalin A concentrations of over 50 mg/(g matrix) can be prepared. Hence the usable concentration range can be extended 100-fold. This is of particular importance for applications wherein the analyte concentration is fixed and cannot be adjusted by dilution or concentration. Precisely such difficulties arise with in vivo applications such as the determination of the glucose level in body fluids. In the in vivo situation, the concentration of the analyte glucose cannot be adjusted to the specific assay conditions, but must rather be taken as given.

A further solubility problem arises in particular with in vivo applications of biological sensors. Owing to the higher wavelength, the intrinsic fluorescence of the tissue declines, so that with in vivo applications long wavelength fluorescent dyes are used. However, these fluorescent dyes are typically apolar owing to their molecular structure and size (conjugated systems). If the glucose-binding protein is only labeled with such a dye, the solubility further decreases, so that high degrees of labeling are also not possible. As already described above, it can therefore be necessary to functionalize the glucose-binding protein with e.g. polyethylene glycol, in order to enable increased solubility and higher degrees of labeling associated therewith. However, functionalization with polyethylene glycol (pegylation) as a rule leads to a markedly reduced glucose activity of for example native concanavalin A (relative glucose activity of 0.4 or less). Surprisingly, in the context of the present invention it was established that in the hydrogel of the sensor device this worsening does not occur. Rather, glucose activities for concanavalin A functionalized with polyethylene glycol can be achieved which are comparable with those of native concanavalin A (relative glucose activity=2.2 or 2.6). Furthermore, it was found that the glucose activity can be still further raised by increasing the degree of labeling on the concanavalin A in a hydrogel such as is used in the device of the present invention. Thus, surprisingly, in the enriching hydrogel, by increasing the degree of labeling on the concanavalin A functionalized with polyethylene glycol, a doubling of the glucose activity could even be achieved. Compared to the measurement in solution, the glucose activity in the hydrogel used according to the invention in the sensor device is even increased 4.3-fold. The use of the hydrogel in the device according to the invention thus makes it possible to prepare concentration ratios for the glucose-binding protein and its ligand which with equivalent degrees of labeling allow glucose activities which are increased 4-fold compared to concentrations which are preparable in aqueous solutions. This advantageously also enables the use of the device according to the invention under conditions wherein the analyte concentration cannot be adapted to the assay conditions, such as with in vivo applications.

In the context of the use according to the present invention, the sensor can preferably be used for determining glucose content.

Thereby, a sample can be tested. In the context of the present invention, the term "sample" should be understood to mean a composition, preferably an aqueous composition, which presumably or actually contains glucose. The sample is preferably a biological sample. Quite particularly preferably, the sample is a body fluid, in particular tissue fluid (interstitial fluid), blood, plasma, serum, lymph, saliva, tear fluid, sweat or urine. Particularly preferably, the sample is tissue fluid, blood, serum or plasma.

Provided that the sample is a biological material, e.g. a body fluid, it can preferably be obtained from a test subject who either actually or presumably has impaired glucose metabolism. Preferably here, the impaired glucose metabolism is caused by diabetes mellitus or metabolic syndrome.

The sensor can thus also be used in the context of the use according to the invention for ex vivo diagnosis of diseases or impairments of the glucose metabolism. In particular, the sensor can be used for the diagnosis of impaired glucose metabolism and connected therewith of diseases such as diabetes mellitus or metabolic syndrome, or for determining the need for a therapeutic measure in a patient with impaired glucose metabolism.

The aforesaid therapeutic measures comprise those which are used for the treatment of diabetes mellitus or metabolic syndrome. As well as the administration of drugs, e.g. insulin, this also includes the implementation of other therapeutic measures concerning which a decision can be taken on the basis of the impaired glucose metabolism determined. These include therapeutic interventions, e.g. gastric bypass operations, or changes in lifestyle, e.g. the implementation of special diets. The sensor can be coupled with a further device, e.g. a device which controls the delivery of a drug. In this, a device which controls the delivery of insulin is preferable. The delivery of insulin can then be controlled on the basis of the need determined by the sensor.

For ex vivo use, the sensor from the use according to the invention can for example be introduced into microtiter plates and anchored there. Samples for assay are then applied into the wells of the microtiter plates and can then be assayed with a reader device. Such an approach enables the simultaneous assay of a large number of samples and is thus also economical, in particular in clinical diagnostic practice.

Alternatively, the sensor for the in vivo use can be introduced into the body. Here it should be noted that the measurement of the glucose level, which is of course also the basis for the diagnosis, requires that the device come into contact with a body fluid which contains glucose, wherein the concentration of glucose in the fluid is representative of the glucose level to be determined. Suitable body fluids are enumerated at another place in the description. Particularly preferably, the body fluid is tissue fluid.

The sensor is preferably introduced at places in the body which allow optical measurement of the signal generated by the device. Places with either a small tissue thickness between device and body surface or with transparent tissues which can be effectively penetrated by the generated signal are suitable. Particularly preferably, the device is positioned under the skin (subcutaneously) or in the eye, e.g. subconjunctivally. Appropriate methods for the implantation of the device are known in the state of the art.

Alternatively, the signal created by the device according to the invention can also be transferred outside the body by means of a suitable transfer medium. For this, a signal-conducting material can preferably be used as flexible cable, e.g. a glass fiber cable. However, the transfer of the signal can also be effected wirelessly, e.g. as an infrared, radio or wireless signal. It goes without saying that in this case the signal created by the device according to the invention must firstly be read by a detector which must likewise be installed in the device or at least in spatial proximity and be converted into an electromagnetic signal, for example a wireless signal. This electromagnetic signal can then be received by a receiver lying outside the body and evaluated.

Through the use according to the invention of the hydrogel in the sensor, efficient ex vivo and in vivo diagnosis of the blood sugar level is enabled, and hence the early recognition of diseases which are associated with impaired glucose metabolism, and also the management thereof, and the selection of therapeutic measures.

The invention is illustrated by the following practical examples. However, the examples do not limit the protection range.

EXAMPLES

Example 1

Preparation of Sensors for Determining Glucose

Preparation of Hydrogel Particles (Enriching Matrix)

1 g of sodium alginate is dissolved in 100 g water with stirring. 66.2 g of CaCl2×2H2O are dissolved in 4931.3 g water in a 5 L beaker.

The alginate solution is passed into a dual nozzle via a pump. At the same time, compressed air is connected to the second inlet of the nozzle, so that the alginate solution is atomized into fine droplets. The droplets are carried by the air flow into a bath containing the calcium chloride solution, where they gel and sink to the bottom. The gelled beads are then collected.

Preparation of Sensors in Enriching Matrix:

For loading, alginate beads are successively incubated in a dye-labeled concanavalin A solution and a dye-labeled dextran solution. The loaded beads are then centrifuged down and the supernatant solution decanted off. The loaded beads are optionally then incubated overnight in a solution of a second polymer (e.g. PVA or PEG-based) and optionally isolated by centrifugation. The beads are then mixed into an aqueous solution of a photochemically crosslinkable polymer. This mixture is then crosslinked with UV light in order to prevent the sensor components leaching out of the alginate beads.

The quantities for this depend on the concentration of the analyte to be measured and the degree of labeling is selected depending on the desired intensity of the fluorescence signal. As the photochemically crosslinkable polymer, for example Nelfilcon polymer, a polyvinyl alcohol modified with acrylamide groups, can be used. For the photochemical crosslinking, 0.1% Irgacure 2959 is also added. The finished solution is dispensed into suitable molds and cured with UV light.

Preparation of Sensors in Non-Enriching Matrix:

Dye-labeled concanavalin A solution and dye-labeled dextran solution are successively fed into a water-based prepolymer mixture and stirred for 3 hours. The quantities for this depend on the concentration of the analyte to be measured and the degree of labeling is selected depending on the desired intensity of the fluorescence signal. As the photochemically crosslinkable polymer, for example Nelfilcon polymer, a polyvinyl alcohol modified with acrylamide groups, can be used. For the photochemical crosslinking, 0.1% Irgacure 2959 is also added. The finished solution is dispensed into suitable molds and cured with UV light.

Example 2

Determination of the Glucose Activity for the Sensors

Determination of the Glucose Activity in Sensors

The fluorescence spectrum of the sensors is determined at various glucose concentrations. The change in the fluorescence intensities of the donor with increasing glucose content serves as a measure of the quality of the glucose sensor. Since with an in vivo glucose sensor glucose concentrations between 50 and 500 mg/dL have to be measured, the glucose activity is calculated as follows:

$$GA = (\text{intensity}_{500\,mg/dL} - \text{intensity}_{50\,mg/dL}) / \text{intensity}_{50\,mg/dL}$$

For better comparison, all response values are normalized to the response of the same system in solution. For the determination of the relative glucose activity, the glucose activity of the sensor (in matrix) is divided by the glucose activity in solution.

$$\text{Rel } GA = GA(\text{matrix})/GA(\text{solution})$$

Determination of the Glucose Activity in Solution:

Con A solution and dextran solution are diluted in buffer solution and stirred for several hours. The fluorescence spectrum of the solution is determined at various glucose concentrations. The change in the fluorescence intensities of the donor with increasing glucose content serves as a measure of the quality of the system. Since with an in vivo glucose sensor glucose concentrations between 50 and 500 mg/dL have to be measured, the glucose activity is calculated as follows:

$$GA = (\text{intensity}_{500\,mg/dL} - \text{intensity}_{50\,mg/dL}) / \text{intensity}_{50\,mg/dL}$$

Example 3

Determination of the Influence of the Matrix

According to the invention, the glucose-binding protein and the ligand are incorporated into a hydrogel matrix which exhibits a certain interaction with the glucose-binding protein. For this, the hydrogel matrix is selected such that firstly the interaction of glucose-binding protein and hydrogel matrix is greater than that between glucose-binding protein and aqueous solution (enrichment of the sensor components). On the other hand, however, the interaction between glucose-binding protein and the analyte (glucose) must be unaffected or not significantly affected by the interaction of glucose-binding protein and hydrogel matrix.

With suitable selection of the hydrogel matrix, through the interaction between glucose-binding protein and hydrogel matrix an enrichment of the glucose-binding proteins in the matrix far above the solubility limit of the glucose-binding protein in aqueous solution is achieved. In the case of Con A, for example up to 10 times higher concentrations can be achieved than in free solution. The solubility problems become still more extreme after addition of the ligand (e.g. dextran), since the glucose-binding protein-ligand complex exhibits lower solubility owing to its size and often also owing to multivalences. While the Con A-dextran complex in solution at a mass ratio of 1:10 already begins to precipitate beyond a Con A concentration of 0.5 mg/g, Con A concentrations of over 50 mg/g can be prepared in a suitable hydrogel matrix at the same mass ratio. Through the hydrogel matrix, the usable concentration range of the glucose-binding protein, e.g. Con A, can be increased 100-fold.

Since with an in vivo application the range of the analyte concentration is fixed and cannot be adjusted e.g. by dilution or concentration, the concentrations of glucose-binding protein and ligand must be adapted to the in vivo concentration range of the analyte. However, there is often the difficulty that glucose-binding protein concentrations and/or ligand concentrations which exceed the solubility limit would therefore be necessary.

For example, with the Con A-dextran system, in solution a Con A concentration of only 0.5 mg/g can be established at a mass ratio (dex:Con A) of 1:10, since otherwise the Con A-dextran complex begins to precipitate. Here, for the determination of the relative glucose activity (rel GA), the glucose activity (GA) achieved at this concentration is set equal to 1. As expected, in a non-enriching matrix the glucose activity is decreased to half (rel GA=0.52) owing to the lower mobility of the sensor components. In enriching matrix, with the same concentration almost the same response as in solution is obtained (rel GA=0.83). However, significantly higher Con A concentrations can also be prepared in the enriching matrix. At a Con A concentration of 10 mg/g, a 2.6-fold increased glucose activity is obtained in enriching hydrogel matrix (see table 1).

TABLE 1

Influence of the matrix

|  | in solution | in non-enriching matrix | in enriching matrix | in enriching matrix |
|---|---|---|---|---|
| Con A concentration | 0.5 mg/g | 0.5 mg/g | 0.5 mg/g | 10 mg/g |
| Rel GA | 1 | 0.52 | 0.83 | 2.55 |

Native Con A with DOL = 1, dextran with 0.001 mol dye (D) per mol dex subunit (SU), mass ratio dex:Con A = 1:10

Example 4

Determination of the Influence of the Concentration of the Receptor

In enriching matrix, a dependence of the glucose activity on the starting concentration of the glucose-binding protein and of the ligand is clearly seen. With a rise in the concentration, a rise in the glucose activity is also obtained. At very high receptor concentrations, the glucose activity again declines. The optimal Con A concentration for an in vivo assay lies between 8 and 20 mg Con A/g matrix (see table 2).

TABLE 2

Influence of the receptor concentration

| | Con A conc. [mg/g] | | | | |
|---|---|---|---|---|---|
| | 0.5 | 10.0 | 13.3 | 30 | 52.2 |
| Relative Glucose activity (rel GA) | 0.83 | 2.55 | 2.76 | 2.14 | 1.76 |

Native Con A with DOL = 1, dextran with 0.001 mol dye (D) per mol dex subunit (SU), mass ratio dex:Con A = 1:10

Example 5

Determination of the Influence of the degree of Labeling Receptor

Owing to the decreasing intrinsic fluorescence of the tissue with higher wavelengths, long wavelength fluorescent dyes must be used with in vivo applications. These fluorescent dyes are typically quite nonpolar owing to the larger conjugated system. If the glucose-binding protein is labeled with such dyes, then its solubility decreases, so that high degrees of labeling are often not possible owing to precipitation. In order to increase the solubility of the glucose-binding protein, it is advantageous to functionalize this e.g. with polyethylene glycol. Thereby, the solubility of the glucose-binding protein increases, as a result of which higher degrees of labeling are possible in the synthesis.

However, pegylated Con As in solution lead to only less than half of the glucose activity of native Con A (rel GA=0.4). Surprisingly, in the hydrogel matrix this worsening does not arise. With PEG-Con A, comparable glucose activity to that with native Con A is obtained (rel GA=2.2 vs. 2.6) (see table 3).

TABLE 3

Influence of the degree of labeling (DOL)

| | | DOL Con A | |
|---|---|---|---|
| | | 1 | 1 |
| Type | | native | pegylated |
| Solution, c = 0.5 mg Con A/g | rel GA | 1 | 0.43 |
| Matrix, c = 10 mg Con A/g | rel GA | 2.55 | 2.22 |

Through the pegylation, it first becomes possible to equip Con A with a high degree of labeling with a long wavelength fluorescent dye which is in the long-term stable in solution and does not precipitate. Surprisingly, no worsening of the glucose activity due to the pegylation is observed in enriching matrix compared to in solution. Hence, only through the positive effect of the matrix is it possible to use PEG-Con A with a high degree of labeling at high concentrations in an assay.

Astonishingly, the glucose activity can be further increased by increasing the degree of labeling on the Con A. In the enriching hydrogel matrix, with Con A with DOL=2.5, almost a doubling of the glucose activity is achieved (rel GA=4.3 vs. 2.6). In direct comparison to the measurement in solution, the glucose activity in matrix is thus even increased 4.3-fold through the combined effect of concentration and DOL (see table 4).

TABLE 4

Influence of the degree of labeling (DOL)

| | | DOL Con A | | | |
|---|---|---|---|---|---|
| | | 1 | 1 | 2.5* | 2.5 |
| Type | | native | pegylated | native* | pegylated |
| Solution, c = 0.5 mg Con A/g | rel GA | 1 | 0.43 | | 1.03 |
| Matrix, c = 10 mg Con A/g | rel GA | 2.55 | 2.22 | | 4.28 |

*native ATTO680-Con A with a DOL of >1.5 is not stable in solution and precipitates.

Example 6

Determination of the Influence of the Fluorescent Dyes

The structure of the fluorescent dyes which are bound to glucose-binding protein and ligand respectively also has an influence on the glucose activity. A combination of a rhodamine and an oxazine dye has proved particularly suitable. For the Con A-dextran system, a rhodamine donor (e.g. ATTO590- or ATTO610-dextran or ROX-dextran) and an oxazine acceptor (e.g. ATTO655- or ATTO680-Con A, or Evoblue30-Con A) is particularly preferable. Thereby, in contrast to the conventionally used TMR-Con A/FITC-dextran system (xanthene-rhodamine combination), a 2.1-fold glucose activity in solution and even 2.6-fold in enriching matrix is obtained. With a rhodamine-oxazine dye pair, a heterodimer interaction can arise between the dyes which intensifies the glucose activity (see tables 5 and 6).

TABLE 5

Influence of the dyes

| Con A-dye | | ATTO680 | TMR |
|---|---|---|---|
| Dextran-dye | | ATTO590 | FITC |
| DOL Con A | | 2.5* | 2.3 |
| Type | | native* | native |
| Solution, c = 0.5 mg Con A/g | rel GA | 2.4 | 1.17 |
| Relative activity compared to the conventional system FITC/TMR | | 2.05 | 1 |
| Matrix, c = 10 mg Con A/g | rel GA | 4.92 | 1.9 |
| Relative activity compared to the conventional system FITC/TMR | | 2.59 | 1 |

Corresponding values extrapolated on the basis of the experimental values with PEG-Con A: FITC-dextran with 0.01 mol D/mol SU, mass ratio dex:Con A = 1:10

TABLE 6

Influence of the dyes

| | | ATTO590/ATTO680 | ROX/Evoblue30 |
|---|---|---|---|
| Matrix, c = 10 mg Con A/g | rel GA | 2.55 | 2.1 |

Native Con A with DOL = 1, dextran with 0.001 mol dye (D) per mol dex subunit (SU), mass ratio dex:Con A = 1:10

Example 7

Determination of the Influence of the Nature of the Hydrogel Matrix

The glucose activity is also dependent on the nature of the hydrogel matrix. The hydrogel matrix can consist of one polymer or of a mixture of several polymers. A hydrogel matrix made of alginate or a mixture of an alginate and a polyvinyl alcohol hydrogel has proved advantageous. Through its interaction with the Con A and the dextran, the alginate hydrogel enables the enrichment of the sensor components in high concentrations.

The prepolymer of the $2^{nd}$ hydrogel (e.g. PVA) can penetrate into the alginate beads and after its crosslinking form an interpenetrating network with the alginate. The mesh width of the interpenetrating network influences the mobility of the molecules of the glucose-binding protein and of the ligand and thus also the glucose activity. The mesh width can be influenced through the nature, the molecular weight and the solids content of the polymer and the content of crosslinker groups, which determines the number of junctions.

A lower content of crosslinker groups leads to a higher glucose activity. Through a halving of the crosslinker groups, the activity can even be increased 1.5-fold. Hence, compared to the system in solution, a 4.2-fold improvement in the glucose activity can also be achieved without an increase in the degree of labeling on the Con A (see table 7).

TABLE 7

Influence of the crosslinker content

| | Crosslinker content (mmol/g) | | |
|---|---|---|---|
| | 0.486 | 0.33 | 0.26 |
| Rel GA | 2.76 | 4.04 | 4.24 |

Native Con A (13 mg/g) with DOL = 1, dextran with 0.001 mol dye (D) per mol dex subunit (SU), mass ratio dex:Con A = 1:10

The solids content of the network also has an influence on the glucose activity. The higher the solids content, the lower is the glucose activity (see table 8).

TABLE 8

Influence of the solids content

| | SC Prepolymer | | | |
|---|---|---|---|---|
| | 25% | 30% | 35% | 40% |
| Rel. GA | 2.87 | 2.76 | 2.48 | 1.96 |

Native Con A (13 mg/g) with DOL = 1, dextran with 0.001 mol dye (D) per mol dex subunit (SU), mass ratio dex:Con A = 1:10

The invention claimed is:

1. A method for enriching a dissolved glucose-binding protein in a hydrogel, comprising:
  (a) providing a polymer-based hydrogel comprising at least one water-soluble polymer, wherein the polymer-based hydrogel comprises a first hydrogel matrix and a second hydrogel matrix which forms an interpenetrating network within the first hydrogel matrix; and
  (b) incorporating a glucose-binding protein and a ligand binding to the glucose-binding protein into the polymer-based hydrogel of step (a), wherein (i) the at least one water-soluble polymer is capable of interacting with the glucose-binding protein, and (ii) the glucose-binding protein is present in a complex with the ligand, thereby enriching the dissolved glucose-binding protein in the hydrogel.

2. The method of claim 1, wherein the ligand of the glucose-binding protein is an oligosaccharide, a glycosylated macromolecule, or a glycosylated nanoparticle.

3. The method of claim 1, wherein the dissolved glucose-binding protein is present at an at least 5-fold, at least 10-fold, at least 15-fold, or at least 20-fold elevated concentration as compared to an aqueous solution.

4. The method of claim 1, wherein the at least one polymer is selected from the group consisting of alginates, sepharose, hyaluronic acid, chitosan, and caragenans.

5. The method of claim 1, wherein the polymer-based hydrogel comprises a first hydrogel matrix comprising alginate and a second hydrogel matrix which forms an interpenetrating network within the first hydrogel matrix.

6. The method of claim 1, wherein the glucose-binding protein is selected from the group consisting of lectins, enzymes which bind glucose as substrate, antibodies which specifically recognize glucose, and aptamers which specifically recognize glucose.

7. The method of claim 1, wherein the glucose-binding protein is concanavalin A.

8. The method of claim 7, wherein the concanavalin A concentration is greater than about 0.5 mg/(g polymer).

9. The method of claim 8, wherein the concanavalin A concentration lies between about 2 and about 60 mg/(g polymer).

10. The method of claim 7, wherein the concanavalin A exhibits increased water solubility as compared to unmodified concanavalin A owing to chemical modification.

11. The method of claim 10, wherein the modification is selected from the group consisting of: pegylation, acetylation, succinylation, and polyoxazolinylation.

12. The method of claim 2, wherein the glucose-binding protein is linked to an oxazine dye and the ligand of the glucose-binding protein is linked to a rhodamine dye.

* * * * *